United States Patent
Kosley, Jr. et al.

[11] Patent Number: 5,646,300
[45] Date of Patent: Jul. 8, 1997

[54] (1H-INDOL-1-YL)-2-(AMINO)ACETAMIDES AND RELATED (1H-INDOL-1-YL)-(AMINOALKYL)AMIDES, PHARMACEUTICAL COMPOSITION AND USE

[75] Inventors: Raymond W. Kosley, Jr.; Denise M. Flanagan, both of Bridgewater; Lawrence L. Martin, Lebanon; Peter A. Nemoto, Piscataway, all of N.J.

[73] Assignee: Hoechst Marion Roussel, Inc., Cincinnati, Ohio

[21] Appl. No.: 457,649

[22] Filed: Jun. 1, 1995

Related U.S. Application Data

[62] Division of Ser. No. 218,211, Mar. 25, 1994, which is a division of Ser. No. 863,273, Apr. 3, 1992, Pat. No. 5,319,096.

[51] Int. Cl.$^6$ .................. C07D 209/10; C07D 493/04
[52] U.S. Cl. ............................. 548/475; 548/430
[58] Field of Search .................... 548/475, 430

*Primary Examiner*—David B. Springer
*Attorney, Agent, or Firm*—Barbara V. Maurer; Barbara E. Kurys

[57] ABSTRACT

There are disclosed neuroprotective compounds having the formula

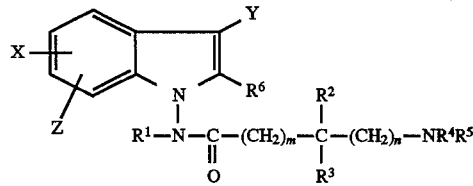

wherein the moieties are defined in the specification, and processes for making them.

2 Claims, No Drawings

5,646,300

(1H-INDOL-1-YL)-2-(AMINO)ACETAMIDES AND RELATED (1H-INDOL-1-YL)-(AMINOALKYL)AMIDES, PHARMACEUTICAL COMPOSITION AND USE

This is a division of a pending prior application Ser. No. 08/218,211, filed Mar. 25, 1994, which is a divisional of a prior application Ser. No. 07/863,273, filed Apr. 3, 1994, U.S. Pat. No. 5,319,096.

This invention relates to compounds having the formula

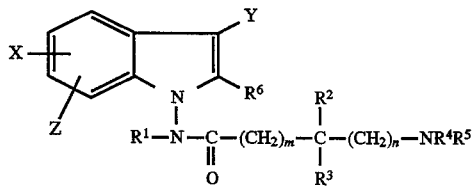

wherein

X is hydrogen, chloro, bromo, fluoro, hydroxy, loweralkoxy, arylloweralkoxy, acyloxy, loweralkylaminocarbonyloxy, diloweralkylaminocarbonyloxy, amino, loweralkylamino, diloweralkylamino, acylamino, loweralkyl or trifluoromethyl;

Y is hydrogen, loweralkyl, chloro or bromo;

Z is hydrogen, loweralkyl, loweralkoxy or halogen; or X and Z taken together can form a methylenedioxy group;

$R^1$ is hydrogen, loweralkyl, arylloweralkyl, carboxyloweralkyl, arylloweralkoxycarbonylloweralkyl or loweralkoxycarbonylloweralkyl;

$R^2$ is hydrogen, loweralkyl or hydroxyloweralkyl;

$R^3$ is hydrogen or loweralkyl; or $R^2$ and $R^3$ together with the carbon to which they are attached form $(C_3-C_7)$cycloalkyl;

$R^4$ is hydrogen or loweralkyl; $R^5$ is hydrogen, loweralkyl, aryl, arylloweralkyl, acyl, arylloweralkoxycarbonyl, loweralkoxycarbonyl or aryloxycarbonyl;

$R^6$ is hydrogen, chloro, bromo, arylcarbonyl, loweralkylcarbonyl, aryl(hydroxy)alkyl or hydroxyalkyl; and m and n are independently 0 to 5 with the proviso that the sum of m plus n is not greater than 5 and pharmaceutically acceptable addition salts thereof, or where applicable, the optical or geometrical isomers or racemic mixtures thereof.

This invention also relates to pharmaceutical compositions of the compounds and a method of use as neuroprotective agents, a process for making the compounds and intermediate compounds used in the process.

Throughout the specification and the appended claims, a given chemical formula or name shall encompass all stereo, geometrical and optical isomers thereof where such isomers exist, as well as pharmaceutically acceptable acid addition salts thereof.

The following definitions shall apply throughout the specification and the appended claims.

Unless otherwise stated or indicated, the term loweralkyl denotes a straight or branched alkyl group having from 1 to 6 carbon atoms, such as, for example, methyl, ethyl, n-propyl, isopropyl, isobutyl, n-butyl, t-butyl, sec-butyl, pentyl and hexyl.

Unless otherwise stated or indicated, the term cycloalkyl denotes an alicyclic hydrocarbon group containing 3 to 7 carbon atoms such as, for example, cyclopropyl, cyclopentyl, cyclohexyl and cycloheptyl.

Unless otherwise stated or indicated the term halogen means fluorine, chlorine, bromine or iodine.

Unless otherwise stated or indicated, the term aryl shall mean unsubstituted phenyl or phenyl substituted with 1, 2 or 3 substituents independently selected from loweralkyl, halogen, trifluoromethyl, loweralkoxy or hydroxy.

Unless otherwise stated or indicated, the term acyl shall mean formyl or loweralkylcarbonyl such as, for example, methylcarbonyl (acetyl).

In a preferred embodiment of this invention are compounds of the formula

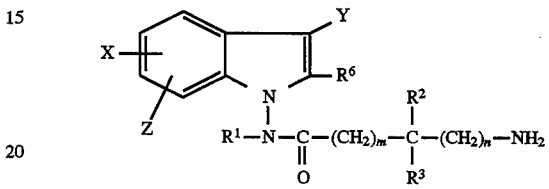

wherein

X is hydrogen, chloro, bromo, fluoro, hydroxy, loweralkoxy, arylloweralkoxy, acyloxy, loweralkylaminocarbonyloxy, diloweralkylaminocarbonyloxy, amino, loweralkylamino, diloweralkylamino, acylamino, loweralkyl or trifluoromethyl;

Y is hydrogen, loweralkyl, chloro or bromo;

Z is hydrogen, loweralkyl, loweralkoxy or halogen; or X and Z taken together can form a methylenedioxy group;

$R^1$ is hydrogen, loweralkyl, arylloweralkyl, carboxyloweralkyl, arylloweralkoxycarbonylloweralkyl or loweralkoxycarbonylloweralkyl;

$R^2$ is hydrogen, loweralkyl or hydroxyloweralkyl;

$R^3$ is hydrogen or loweralkyl; or $R^2$ and $R^3$ together with the carbon to which they are attached form $(C_3-C_7)$cycloalkyl;

$R^6$ is hydrogen, chloro, bromo, arylcarbonyl, loweralkylcarbonyl, aryl(hydroxy)loweralkyl or hydroxyloweralkyl;

m and n are independently 0 to 2; and pharmaceutically acceptable salts thereof.

More preferably

X is hydrogen, chloro, hydroxy, methoxy, phenylmethoxy or N-methylaminocarbonyloxy;

Y is hydrogen, chloro or methyl;

Z is hydrogen;

$R^1$ is hydrogen, methyl or carboxymethyl;

$R^2$ is hydrogen, methyl or hydroxymethyl;

$R^3$ is hydrogen;

$R^6$ is hydrogen, chloro, bromo, methylcarbonyl, phenylcarbonyl, halophenylcarbonyl, methoxyphenylcarbonyl, methylphenylcarbonyl or (trifluoromethylphenyl)carbonyl; and m and n are independently 0 or 1; and pharmaceutically acceptable salts thereof.

Most preferable are compounds of this embodiment wherein

X is hydrogen, 5-chloro, 5-methoxy, 5-phenylmethoxy or 5-(N-methylaminocarbonyloxy);

Y is hydrogen or methyl;

$R^1$ is hydrogen, methyl or carboxymethyl;

$R^2$ is hydrogen, methyl or hydroxymethyl;

$R^3$ is hydrogen;

$R^6$ is hydrogen, chloro, bromo, methylcarbonyl, phenylcarbonyl, (2-methylphenyl)carbonyl, (2-methoxyphenyl)carbonyl, (2-fluorophenyl)carbonyl, (4-fluorophenyl)carbonyl, (3-fluorophenyl)carbonyl or (2-trifluoromethylphenyl)carbonyl;

m and n are each 0; and hydrochloride salts thereof.

In another preferred embodiment of the inventions are compounds of the formula

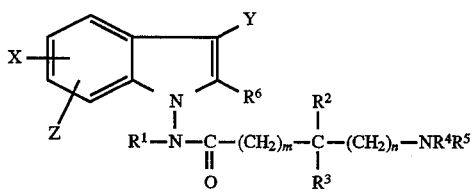

wherein

X is hydrogen, chloro, bromo, fluoro, hydroxy, loweralkoxy, arylloweralkoxy, acyloxy, loweralkylaminocarbonyloxy, diloweralkylaminocarbonyloxy, amino, loweralkylamino, diloweralkylamino, acylamino, loweralkyl or trifluoromethyl;

Y is hydrogen, loweralkyl, chloro or bromo;

Z is hydrogen, loweralkyl, loweralkoxy or halogen; or X and Z taken together can form a methylenedioxy group;

$R^1$ is hydrogen, loweralkyl, arylloweralkyl, carboxyloweralkyl, arylloweralkoxycarbonylloweralkyl or loweralkoxycarbonylloweralkyl;

$R^2$ is hydrogen, loweralkyl or hydroxyloweralkyl;

$R^3$ is hydrogen or loweralkyl; or $R^2$ and $R^3$ together with the carbon to which they are attached form $(C_3-C_7)$cycloalkyl;

$R^4$ is hydrogen or loweralkyl;

$R^5$ is hydrogen, loweralkyl, aryl, arylloweralkyl, acyl, arylloweralkoxycarbonyl, loweralkoxycarbonyl or aryloxycarbonyl; provided $R^4$ and $R^5$ are not simultaneously hydrogen;

$R^6$ is hydrogen, chloro, bromo, arylcarbonyl, loweralkylcarbonyl, aryl(hydroxy)loweralkyl or hydroxyloweralkyl; and m and n are independently 0 to 2; and pharmaceutically acceptable addition salts thereof or, where applicable, the optical or geometrical isomers or racemic mixtures thereof.

More preferably

X is hydrogen, chloro, hydroxy, methoxy, phenylmethoxy or N-methylaminocarbonyloxy;

Y is hydrogen or methyl;

Z is hydrogen;

$R^1$ is hydrogen, methyl or phenylmethoxycarbonylloweralkyl;

$R^2$ is hydrogen, methyl or hydroxymethyl;

$R^3$ is hydrogen;

$R^4$ is hydrogen or methyl;

$R^5$ is loweralkoxycarbonyl or arylloweralkoxycarbonyl;

$R^6$ is hydrogen, chloro, bromo, methylcarbonyl, phenylcarbonyl, loweralkylphenylcarbonyl, halophenylcarbonyl, loweralkoxyphenylcarbonyl or trifluoromethylphenylcarbonyl;

m and n are independently 0 or 1; and pharmaceutically acceptable salts thereof.

Most preferable are compounds of this embodiment wherein

X is hydrogen, 5-chloro, 5-hydroxy, 5-methoxy, 5-phenylmethoxy or 5-(N-methylaminocarbonyloxy);

Y is hydrogen or methyl;

$R^1$ is hydrogen, methyl or phenylmethyoxycarbonylmethyl;

$R^2$ is hydrogen, methyl or hydroxymethyl;

$R^3$ is hydrogen;

$R^4$ is hydrogen;

$R^5$ is t-butoxycarbonyl or phenylmethoxycarbonyl;

$R^6$ is hydrogen, chloro, bromo, methylcarbonyl, phenylcarbonyl, (2-methylphenyl)carbonyl, (2-methoxyphenyl)carbonyl, (2-fluorophenyl)carbonyl, (4-fluorophenyl)carbonyl, (3-fluorophenyl)carbonyl, or (2-trifluoromethylphenyl)carbonyl.

m and n are each 0; and pharmaceutically acceptable salts thereof.

Also encompassed by this invention are intermediate compounds of the formula

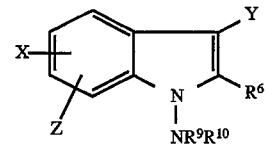

wherein

X is hydrogen, chloro, bromo, fluoro, hydroxy, loweralkoxy, arylloweralkoxy, acyloxy, loweralkylaminocarbonyloxy, diloweralkylaminocarbonyloxy, amino, loweralkylamino, diloweralkylamino, acylamino, loweralkyl or trifluoromethyl;

Y is hydrogen, loweralkyl, chloro or bromo;

Z is hydrogen, loweralkyl, loweralkoxy or halogen; or X and Z taken together can form a methylenedioxy group;

$R^6$ is hydrogen, chloro, bromo, arylcarbonyl, loweralkylcarbonyl, aryl(hydroxy)loweralkyl or hydroxyloweralkyl; and $R^9$ is hydrogen, formyl, loweralkylcarbonyl, loweralkoxycarbonyl, phenylcarbonyl or carboxyphenylcarbonyl; and $R^{10}$ is hydrogen; or $R^9$ and $R^{10}$ together with the nitrogen to which they are attached are phthalimidoyl.

In one embodiment of the intermediates are compounds of the formula

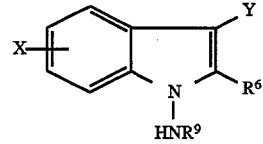

wherein

X is hydrogen, fluoro, hydroxy, loweralkoxy, arylloweralkoxy, acyloxy, loweralkyl or trifluoromethyl;

Y is hydrogen or loweralkyl;

R⁶ is hydrogen, arylcarbonyl, loweralkylcarbonyl, aryl (hydroxy)loweralkyl or hydroxyloweralkyl; and R⁹ is loweralkylcarbonyl, loweralkoxycarbonyl, phenylcarbonyl or carboxyphenylcarbonyl.

More preferably,

X is hydrogen, hydroxy, methoxy or phenylmethoxy;

Y is hydrogen or methyl;

R⁶ is hydrogen, aryl(hydroxy)loweralkyl or hydroxyloweralkyl; and

R⁹ is butylcarbonyl, t-butyoxycarbonyl, phenylcarbonyl or carboxyphenylcarbonyl.

Most preferably,

X is hydrogen, 5-methoxy or 5-phenylmethoxy;

Y is hydrogen or methyl; and

R⁶ is hydrogen, hydroxymethyl or 1-(hydroxy)ethyl; and

R⁹ is t-butylcarbonyl, t-butoxycarbonyl, phenylcarbonyl or carboxyphenylcarbonyl.

In another embodiment of the intermediates are compounds of the formula

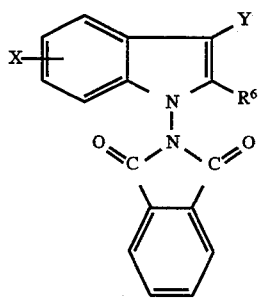

wherein

X is hydrogen, chloro, bromo, fluoro, hydroxy, loweralkoxy, arylloweralkoxy, acyloxy, loweralkyl or trifluoromethyl;

Y is hydrogen or loweralkyl; and

R⁶ is hydrogen, arylcarbonyl or loweralkylcarbonyl.

More preferably,

X is hydrogen, chloro, hydroxy, methoxy or phenylmethoxy;

Y is hydrogen or loweralkyl; and

R⁶ is hydrogen, methylcarbonyl, phenylcarbonyl, halophenylcarbonyl, methoxyphenylcarbonyl, methylphenylcarbonyl or (trifluoromethylphenyl)carbonyl.

Most preferably,

X is hydrogen, 5-chloro, 5-methoxy or 5-phenyhnethoxy;

Y is hydrogen or methyl; and

R⁶ is hydrogen, methylcarbonyl, phenylcarbonyl, (2-methylphenyl)carbonyl, (2-methoxyphenyl) carbonyl, (2-fluorophenyl)carbonyl, (4-fluorophenyl) carbonyl, (3-fluorophenyl)carbonyl or (2-trifluoromethylphenyl)carbonyl.

In yet another embodiment of the intermediates are compounds of the formula

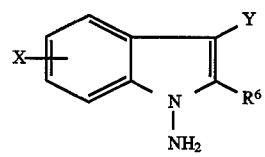

where

X is hydrogen, chloro, bromo, fluoro, hydroxy, loweralkoxy, arylloweralkoxy, acyloxy, loweralkyl or trifluoromethyl;

Y is hydrogen, loweralkyl, chloro or bromo; and

R⁶ is hydrogen, chloro, bromo, arylcarbonyl or loweralkylcarbonyl;

More preferably,

X is hydrogen, chloro, fluoro, hydroxy, methoxy or phenylmethoxy;

Y is hydrogen, methyl, chloro or bromo; and

R⁶ is hydrogen, chloro, bromo, methylcarbonyl, phenylcarbonyl, halophenylcarbonyl, methoxyphenylcarbonyl, methylphenylcarbonyl or trifluoromethylphenylcarbonyl;

Most preferably,

X is hydrogen, 5-chloro, 5-methoxy, 5-hydroxy or 5-phenylmethoxy;

Y is hydrogen, chloro, bromo or methyl; and

R⁶ is hydrogen, chloro, bromo, methylcarbonyl, phenylcarbonyl, (2-methylphenyl)carbonyl; (2-methoxyphenyl)carbonyl, (2-fluorophenyl) carbonyl, (4-fluorophenyl)carbonyl, (3-fluorophenyl) carbonyl or (2-trifluoromethylphenyl)carbonyl.

Examples of compounds of the invention include:

[N-(1H-indol-1-yl)-2-amino]acetamide;
[N-(1H-indol-1-yl)-2-amino]propionamide;
[N-(1H-indol-1-yl)-2-amino-2-(hydroxymethyl)]acetamide;
[N-(3-methyl-1H-indol-1-yl)-2-amino]acetamide;
[N-methyl-N-(1H-indol-1-yl)-2-amino]acetamide;
[N-(2-chloro-3-methyl-1H-indol-1-yl)-2-amino]acetamide;
[N-(5-methoxy-1H-indol-1-yl)-2-amino]acetamide;
[N-(5-phenylmethoxy-1H-indol-1-yl)-2-amino]acetamide;
[N-(5-hydroxy-1H-indol-1-yl)-2-amino]acetamide.
[N-[5-[N-(methyl)aminocarbonyloxy]-1H-indol-1-yl] amino]acetamide;
[N-(2-acetyl-3-methyl-1H-indol-1-yl)-2-amino]acetamide;
[N-(5-chloro-1H-indol-1-yl)-2-amino]acetamide;
[N-(2-(2-fluorobenzoyl)-3-methyl-1H-indol-1-yl)-2-amino] acetamide;
[N-(2-benzoyl-3-methyl-1H-indol-1-yl)-2-amino] acetamide;
[N -(1H-indol-1-yl)-2-(carbamic acid, t-butyl ester)] acetamide;
[N-(1H-indol-1-yl)-2-(carbamic acid, phenylmethyl ester)] acetamide;
[N-(1H-indol-1-yl)2-(carbamic acid, phenylmethyl ester)] acetamide]acetic acid, phenylmethyl ester;
[N-(5-chloro-1H-indol-1-yl)-2-(carbamic acid, t-butyl ester) ]acetamide;
[N-(1H-indol-1-yl)-2-(carbamic acid, phenylmethyl ester)-2-(hydroxymethyl)]acetamide;
[[N-(3-methyl-1H-indol-1-yl)]-2-(carbamic acid, t-butyl ester)]acetamide;
[N-(1H-indol-1-yl)-2-(carbamic acid, t-butyl ester)] propionamide;
[[N-(3-methyl-1H-indol-1-yl)]-2-(carbamic acid, phenylmethyl ester)]acetamide;

[[N-(methyl)-N-(1H-indol-1-yl)]-2-(carbamic acid, phenylmethyl ester)]acetamide;
[[N-(2-chloro-3-methyl-1H-indol-1-yl)]-2-(carbamic acid, phenylmethyl ester)]acetamide;
[[N-(2-chloro-3-methyl-1H-indol-1-yl)]-2-(carbamic acid, t-butyl ester)]acetamide;
[N-(5-methoxy-1H-indol-1-yl)-2-(carbamic acid, phenylmethyl ester)]acetamide;
[N-(5-phenylmethoxy-1H-indol-1-yl)-2-(carbamic acid, phenylmethyl ester)]acetamide;
[N-5-methoxy-3-methyl-1H-indol-1-yl)-2-amino]acetamide;
[N-5-phenylmethoxy-3-methyl-1H-indol-1-yl]-2-amino]acetamide;
[N-5-hydroxy-3-methyl-1H-indol-1-yl]-2-amino]acetamide;
[N-(5-phenylmethoxy-1H-indol-1-yl)-2-(carbamic acid, t-butyl ester)]acetamide;
[N-(5-hydroxy-1H-indol-1-yl)-2-(carbamic acid, phenylmethyl ester)]acetamide;
[N-[5-[N-(methyl)aminocarbonyloxy]-1H-indol-1-yl]-2-(carbamic acid, phenylmethyl ester)]acetamide;
[N-(2-acetyl-3-methyl-1H-indol-1-yl)-2-(carbamic acid, phenylmethyl ester)]acetamide;
[N-[2-(2-fluorobenzoyl)-3-methyl-1H-indol-1-yl]-2-carbamic acid, phenylmethyl ester)]acetamide;
[N-(2-benzoyl-3-methyl-1H-indol-1-yl)-2-(carbamic acid phenylmethyl ester)]acetamide;
[N-(2-benzoyl-3-methyl-1H-indol-1-yl)-2-amino]acetamide;
[N-(1H-indol-1-yl)-2-amino]cyclopropanecarboxamide;
[N-(1H-indol-1-yl)-2-(carbamic acid, t-butyl ester)] cyclopropanecarboxamide;
[N-(1H-indol-1-yl)-2-amino]ethanecarboxamide;
[N-(1H-indol-1-yl)-2-amino]pentanecarboxamide;
[N-(3-methyl-1H-indol-1-yl)-2-amino]ethanecarboxamide;
[N-(3-methyl-1H-indol-1-yl)-2-amino]pentanecarboxamide;
[N-(5,6-dimethoxy-1H-indol-1-yl)-2-amino]acetamide;
[N-(5,7-dimethoxy-1H-indol-1-yl)-2-amino]acetamide;
[N-(5-ethoxy-1H-indol-1-yl)-2-amino]acetamide;
[N-(1 N-(5,6-methylenedioxy-1H-indol-1-yl)-2-amino]acetamide;
[N-(5-methylcarbonylamino-1H-indol-1-yl)-2-amino]acetamide;
[N-(5-dimethylamino-1H-indol-1-yl)-2-amino]acetamide; and
[N-(1H-indol-1-yl)-2-(N-methylcarbamic acid, t-butyl ester)]acetamide.

The compounds of this invention are prepared by using one or more of the steps described in the reaction schemes below. Throughout the description of the synthetic steps, the definitions of X, Y, Z and $R^1$ through $R^6$ are as given above unless otherwise stated or indicated.

More particularly, as shown in Reaction Scheme A, an aminoindole of Formula II is reacted with a compound of Formula III (wherein $R^7$ is loweralkyl or arylloweralkyl) in the presence of a condensing agent such as dicyclohexylcarbodiimide (DCC) to yield a compound of Formula IV, wherein $R^7$ is loweralkyl or arylloweralkyl.

Typically, the reaction is carried out in a suitable solvent such as an aprotic organic solvent, for example, chloroform, dichloromethane, dioxane, or tetrahydrofuran, at a temperature of from about 0° C. to about 100° C., preferably from about 15° C. to about 80° C., more preferably from about 20° C. to about 50° C.

The compound of Formula IV is deprotected by means known in the art. In the case where $R^7$ is phenylmethyl, the compound of Formula IV is deprotected, for example, by treatment with hydrogen in the presence of a catalyst such as palladium on carbon to yield the amino compound of Formula I. The reaction is typically carried out in a polar solvent such as methanol or ethanol at about 0° C. to 50° C., preferably from about 15° C. to about 30° C.

When $R^7$ of Formula IV is t-butyl, the compound is deprotected to yield the corresponding amino compound, for example, by treatment with acid such as hydrochloric acid, hydrobromic acid or trifluoroacetic acid, in an organic solvent such as ethyl acetate, tetrahydrofuran, chloroform and the like, or neat, at from about −50° C. to about 100° C. Preferably, the reaction is carried out in the presence of hydrochloric acid in ethyl acetate at about −15° C. to about 30° C.

In the case where it is preferred that $R^1$ of Formula I is not hydrogen, the compound of Formula IV is reacted with an appropriate alkylating agent, for example, benzyl 2-bromoacetate, benzyl bromide or iodomethane, in the presence of an agent

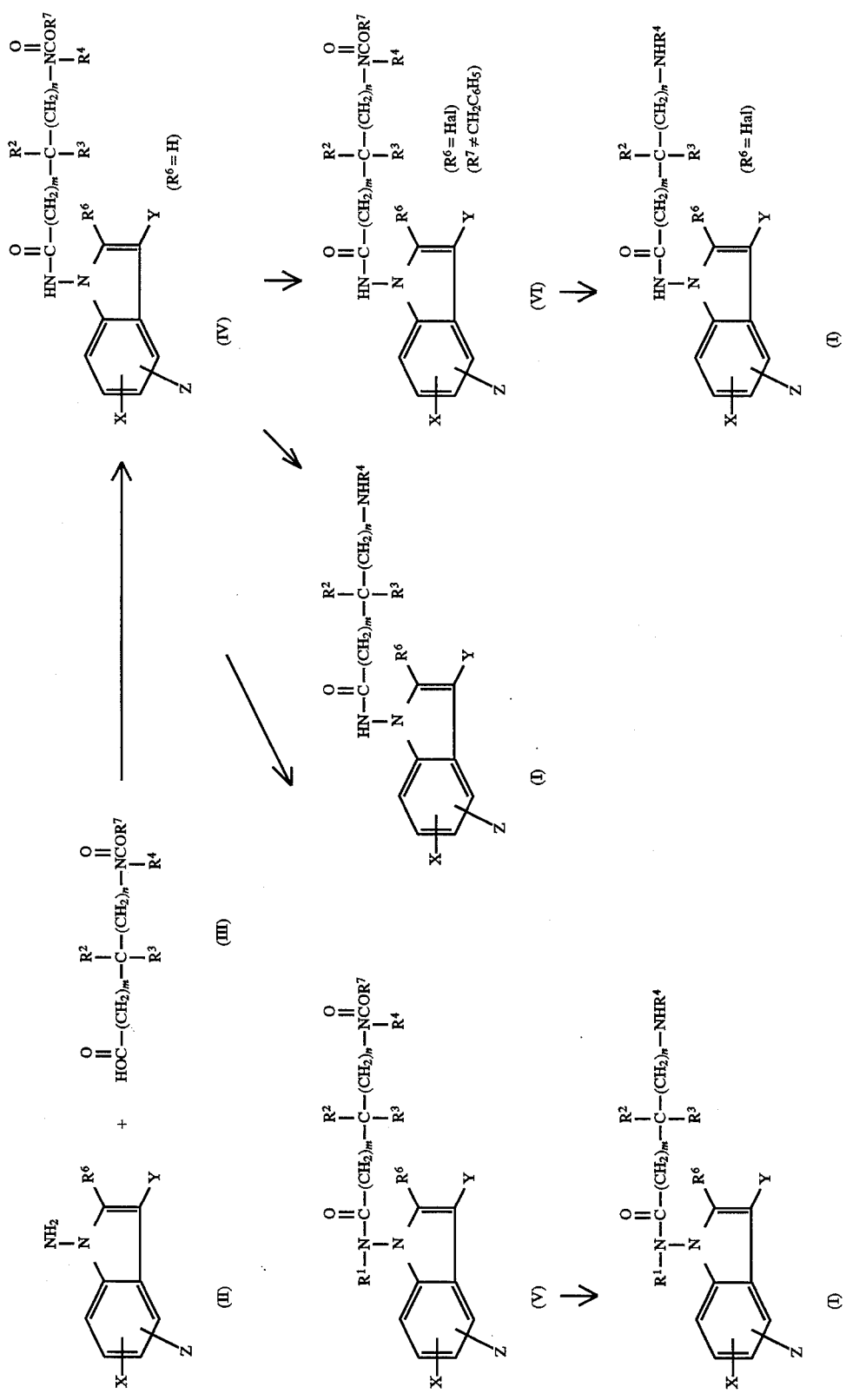

such as 40% KF on alumina or another suitable base to yield a compound of Formula V wherein $R^1$ is not hydrogen.

The reaction is typically carried out in a suitable organic solvent such as acetonitrile at a temperature of from about 0° C. to about 100° C., preferably from about 15° C. to about 80° C., most preferably from about 10° C. to about 50° C.

The compound of Formula V is deprotected essentially as described above to obtain the compound of Formula I wherein $R^1$ is not hydrogen.

The compound of Formula IV where $R^6$ is hydrogen and Y is lower alkyl is reacted with a halogenating agent such as, for example, N-chlorosuccinimide or N-bromosuccinimide, optionally in the presence of a catalyst such as azobis (isobutyronitrile) to obtain a compound of Formula VI wherein $R^6$ is chlorine or bromine. The reaction is generally carried out in a suitable organic solvent such as dimethylformamide at a temperature from about 0° C. to about 100° C., preferably from about 15° C. to about 50° C.

The compound of Formula VI wherein $R^7$ is t-butyl is deprotected to provide the compound of Formula I wherein $R^6$ is halogen, essentially in the same manner as the deprotection of the compound of Formula IV wherein $R^7$ is t-butyl and $R^6$ is hydrogen, to provide the compound of Formula I wherein $R^6$ is hydrogen.

The compounds of Formula II wherein $R^6$ is arylcarbonyl or alkylcarbonyl are prepared from the compound of Formula II wherein $R^6$ is hydrogen as shown in Reaction Scheme B. The compound of Formula II wherein $R^6$ is hydrogen is reacted with phthalic anhydride optionally in the presence of base such as triethylamine to yield a compound of Formula VII. The reaction is generally carried out in a suitable solvent such as, for example, methylene chloride or chloroform at a temperature of from about −30° C. to about 100° C., preferably from about 0° C. to about 65° C.

The compound of Formula VII is treated with a suitable condensing agent such as DCC in the presence of a catalyst such as, for example, dimethylaminopyridine (DMAP) or pyrrolidinopyridine to obtain the phthalimido compound of Formula VIII. The reaction is generally carried out in a suitable solvent such as chloroform at a temperature of from about 0° C. to about 100° C., preferably from about 15° C. to about 50° C.

The compound of Formula VIII is reacted with an acyl halide in the presence of a catalyst, preferably tin (IV) chloride, to yield the corresponding ketone of Formula IX. The reaction is generally carried out in a suitable solvent such as chloroform at a temperature of from about −40° C. to about 80° C., preferably from about −20° C. to about 25° C.

REACTION SCHEME B

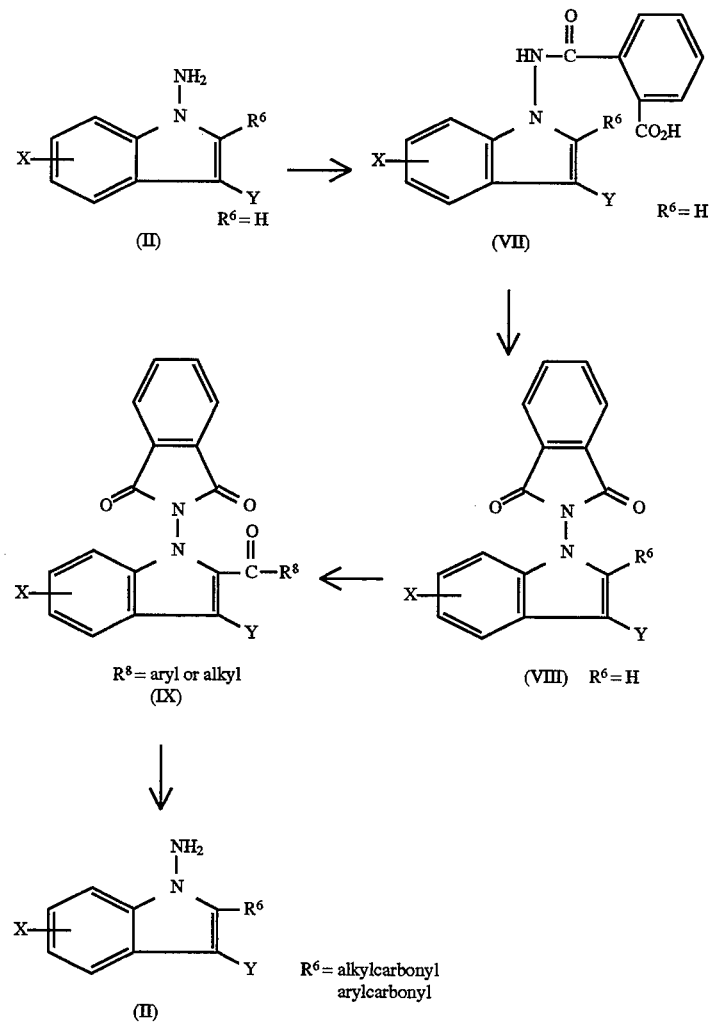

The compound of Formula IX is treated with a suitable base such as, for example, methylamine or hydrazine, preferably methylamine, to remove the phthalimido group, yielding the corresponding 1-aminoindole of Formula II wherein $R^6$ is alkylcarbonyl or arylcarbonyl. The reaction is generally carried out in a polar organic solvent such as, for example, dimethylformamide, from about 0° C. to about 100° C., preferably from about 15° C. to about 50° C., most preferably from about 20° C. to about 50° C.

In addition, as depicted in Reaction Scheme C, compounds of Formula II wherein $R^6$ is hydroxyalkyl or aryl (hydroxy)alkyl are prepared by reacting a compound of Formula II, wherein $R^6$ is hydrogen with trimethylacetyl chloride optionally in the presence of a base such as triethylamine to yield a compound of Formula XI. The reaction is generally carried out in a suitable solvent such as, for example, methylene chloride or chloroform, at a temperature of from about −30° C. to about 100° C., preferably from about 0° C. to about 65° C.

The compound of Formula XI is reacted with an aldehyde in the presence of a base such as, for example, butyllithium to obtain the hydroxy compound of Formula X. The reaction is generally carried out in a suitable solvent such as, for example, dry tetrahydrofuran at a temperature of from about −70° C. to about 100° C., preferably from about −60° C. to about 25° C.

The compound of Formula X is then transformed to the compound of Formula II wherein $R^6$ is hydroxyalkyl or aryl(hydroxy)alkyl.

Hokfelt, T., Elsevier Science Publishers B.V., 1983, pp 508–527). The neurotoxicity of EAA has led to the implication of their involvement in human neurodegenerative disorders such as Alzheimer's Disease. Subacute or chronic overexposure to endogenous neurotoxin may lead to the slow degeneration of neurons (Olney, J., Excitotoxic Amino Acids and Neuropsychiatric Disorders. *Annu. Rev. Pharmacol. Toxicol.* 30:47–71, 1990). Competitive and non-competitive EAA antagonists have been shown to have neuroprotective potential in several animal models. MK-801, a noncompetitive antagonist at the N-methyl-D-aspartate (NMDA) subtype of glutamate receptor, protected against neurodegeneration in the rat striatum caused by intracerebral infusion of NMDA. The competitive NMDA receptor antagonist CPP gave partial protection of striatal neurons when administered (100 mg/kg, i.p.) 1 hour after infusion of quinolinate, a naturally occurring NMDA receptor agonist (Foster, A. C., Gill, R. and Woodruff, G. N., Neuroprotective Effects of MK-801 in vivo: Selectivity and Evidence for Delayed Degeneration Mediated by NMDA Receptor Activation. *J. Neurosci.* 8(12):4745–4754, 1988). 7-Chlorokynurenate and HA-966, two selective antagonists of the glycine site on the NMDA receptor, offer significant neuroprotection against direct infusion of NMDA or quinolinate into the rat striatum (Foster, A. C., Willis, C. L. and Tridgett, R., Protection Against N-methyl-D-aspartate Receptor-Mediated Neuronal Degeneration in Rat Brain by 7-Chlorokynurenate and 3-amino-1-hydroxypyrrolid-2-one, Antagonists at the Allosteric Site for Glycine. *Eur. J. Neu-*

REACTION SCHEME C

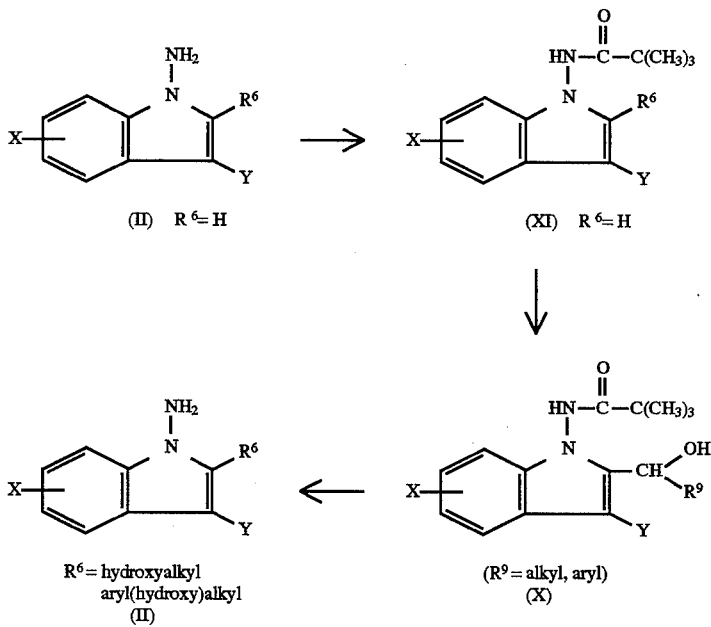

The compounds of the instant invention are useful as neuroprotective agents and as intermediates for making neuroprotective agents.

Glutamate, aspartate and other excitatory amino acids (EAA) are putative neurotransmitters at vertebrate CNS excitatory synapses. This class of neurotransmitters has also been shown to be neurotoxic (Coyle, J. T. and Schwarz, R., The Use of Excitatory Amino Acids as Selective Neurotoxins. In: *Handbook of Chemical Neuroanatomy*, Vol. 1: *Methods in Chemical Neuroanatomy*, ed. Bjorklund, A., and

*rosci.* 2(3):270–277, 1989). NBQX, a selective antagonist at the quisqualate subtype of glutamate receptor, protects against global ischemia in the gerbil (Sheardown, M. J., Nielsen, E. O., Hansen, A. J., Jacobsen, P., Honore, T., 2,3-Dihydroxy-6-nitro-7-sulfamoyl-benzo(F)quinoxaline: A Neuroprotectant for Cerebral Ischemia. *Nature* 247:571–574, 1990). The striatal lesion paradigm can be used to assess the neuroprotective potential of novel compounds.

Testing of the compounds was carried out as follows: Male Sprague Dawley rats (Charles River) are housed under standard laboratory conditions as outlined in the "Guide for the Care and Use of Laboratory Animals" (*National Institutes of Health Publications No.* 85–23, Revised 1985). Food and water were provided ad libitum; lights were on from 0600–1800 h. Sterile techniques were used during surgery.

Rats (250–320 g) were anesthetized with chloral hydrate (400 mg/kg i.p., 10 ml/kg) and mounted in a David Kopf® stereotaxic instrument. An incision was made in the scalp and the skull surface was exposed. All coordinates were taken from the point on the skull where bregma meets the midline suture. The adjustable incisor bar was set at 3.3 mm below horizontal but may be adjusted. A 1–2 mm burr hole in the skull was made with a dental drill 0.5 mm anterior to bregma and 3.0 mm lateral from the midline (Paxinos, G. and Watson, C., *The Rat Brain in Stereotaxic Coordinates*. New York: Academic Press, $2^{nd}$ ed., 1986). A 30-gauge cannula (1 inch length, point #4) was fitted to a 5 μl Hamilton® syringe and was slowly lowered 5.8 mm below the surface of the skull. The cannula remained in place for one minute before infusion began. A total volume of 1 μl of NMDA (150 nanomoles per μl) solution was infused slowly (0.2 μl/2 min, total time of infusion was 10 min). The cannula remained in place for 5 minutes and then was slowly withdrawn (approx. 0.1 mm every 12 sec). NMDA was dissolved in 0.1M sodium phosphate buffer, pH 7.4. An equally osmolar solution of sodium chloride was used as a control in the contralateral striatum. The burr hole was sealed with bone wax and the scalp sutured closed.

The animals were sacrificed by decapitation seven days following surgery. The striatum was dissected over ice. Samples were frozen over dry ice, weighed and then stored at −60° C. until assayed for choline acetyltransferase (ChAT) F. Fonnum, *J. Neurochem.*, 24:407‘409, 1975 and glutamic acid decarboxylase (GAD) (S. H. Wilson et al., *J. Biol. Chem.*, 247:3159–3169, 1972) activities within 1 to 15 days.

The experimental compounds were dissolved in 0.9% NaCl or appropriate vehicle and administered i.p. either pre- and/or post-excitotoxin infusion. Percent control values (TABLE 1) reflect enzyme activity on the left (lesioned side) compared to the contralateral control side of each animal. Analysis of variance was calculated by the Newman-Keuls test with the PHARM/PCS computer program (Tallarida, R. J. and Murray, R. B., *Manual of Pharmacologic Calculations with Computer Programs*, Springer-Verlag, New York, 1987).

TABLE 1

Protection Against NMDA-induced Striatal Lesion

| Treatment | Dose (mg/kg,ip) | Pretreatment Time (min) | % Control Enzyme Activity ChAT | GAD |
|---|---|---|---|---|
| [N-(1H-indol-1-yl)-2-amino] acetamide HCl | 100 | 30 | 68 | 63 |
| Vehicle | — | 60 | 35 | 42 |
| dizocilpine (ref.) | 10 | 60 | 104 | 110 |

Effective quantities of the compounds of the invention may be administered to a patient by any of the various methods, for example, orally as in capsule or tablets, parenterally in the form of sterile solutions or suspensions, and in some cases intravenously in the form of sterile solutions. The free base final products, while effective themselves, may be formulated and administered in the form of their pharmaceutically acceptable acid addition salts for purposes of stability, convenience of crystallization, increased solubility and the like.

Acids useful for preparing the phamaceutically acceptable acid addition salts of the invention include inorganic acids such as hydrochloric, hydrobromic, sulfuric, nitric, phosphoric and perchloric acids, as well as organic acids such as tartaric, citric, acetic, succinic, maleic, fumaric and oxalic acids.

The active compounds of the present invention may be orally administered, for example, with an inert diluent or with an edible carrier, or they may be enclosed in gelatin capsules, or they may be compressed into tablets. For the purpose of oral therapeutic administration, the active compounds of the invention may be incorporated with excipients and used in the form of tablets, troches, capsules, elixirs, suspensions, syrups, wafers, chewing gum and the like. These preparations should contain at least 0.5% of active compounds, but may be varied depending upon the particular form and may conveniently be between 5% to about 70% of the weight of the unit. The amount of active compound in such compositions is such that a suitable dosage will be obtained. Preferred compositions and preparations according to the present invention are prepared so that an oral dosage unit form contains between 1.0–300 milligrams of active compound.

The tablets, pills, capsules, troches and the like may also contain the following ingredients: a binder such as microcrystalline cellulose, gum tragacanth or gelatin; an excipient such as starch or lactose, a disintegrating agent such as alginic acid, Primogel, cornstarch and the like; a lubricant such as magnesium stearate or Sterorex; a glidant such as colloidal silicon dioxide; and a sweeting agent such as sucrose or saccharin may be added or a flavoring agent such as peppermint, methyl salicylate, or orange flavoring. When the dosage unit form is a capsule, it may contain, in addition to materials of the above type, a liquid carrier such as a fatty oil. Other dosage unit forms may contain other various materials which modify the physical form of the dosage unit, for example, as coatings. Thus, tablets or pills may be coated with sugar, shellac, or other enteric coating agents. A syrup may contain, in addition to the active compounds, sucrose as a sweetening agent and certain preservatives, dyes, colorings and flavors. Materials used in preparing these various compositions should be phamaceutically pure and non-toxic in the amounts used.

For the purpose of parenteral therapeutic administration, the active compounds of the invention may be incorporated into a solution or suspension. These preparations should contain at least 0.1% of active compound, but may be varied between 0.5 and about 30% of the weight thereof. The amount of active compound in such compositions is such that a suitable dosage will be obtained. Preferred compositions and preparations according to the present inventions are prepared so that a parenteral dosage unit contains between 0.5 to 100 milligrams of active compound.

The solutions or suspensions may also include the following components: a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfite; chelating agents such as ethylenediaminetetraacetic acid; buffers such as acetates; citrates or phosphates and agents for the adjustment of tonicity such as sodium chloride or dextrose. The parenteral multiple dose vials may be of glass or plastic.

The following examples will further illustrate this invention but are not intended to limit it in anyway. In Table II, typical N-(1H-indol-1-yl)-2-aminoacetamides of the present invention are listed. in Tables III–V, typical intermediates useful in the preparation of the compounds of Table II are listed. Following the Tables, specific illustrative preparations of compounds of the invention are described.

TABLE II $$R^1-N-\underset{\underset{N}{|}}{\overset{\overset{O}{\|}}{C}}-\overset{R^2}{\underset{|}{C}H}-NH_2$$

(indole ring with X substituent, $R^6$ at 2-position, Y at 3-position)

| Ex. | $R^1$ | $R^2$ | $R^6$ | X | Y | salt | mp °C. |
|---|---|---|---|---|---|---|---|
| 1b | H | H | H | H | H | HCl | 260–262d |
| 2b | H | CH₂OH | H | H | H | HCl | 216–220 |
| 3b | CH₂CO₂H | H | H | H | H | — | 212–216d |
| 4b | H | H | H | H | CH₃ | HCl | 260–270d |
| 5b | CH₃ | H | H | H | H | HCl | 253–258 |
| 6c | H | H | Cl | H | CH₃ | HCl | 248–249 |
| 7c | H | H | H | 5-OCH₃ | H | HCl | 229–235 |
| 8c | H | H | H | 5-OCH₂C₆H₅ | H | HCl | 146–150d |
| 9d | H | H | (C=O)CH₃ | H | CH₃ | HCl | 134–165 |
| 10f | H | H | (C=O)C₆H₄-2F | H | CH₃ | HCl | 150–170 |
| 11d | H | H | (C=O)C₆H₄-4F | H | CH₃ | HCl | 160–170 |
| 12d | H | H | (C=O)C₆H₄-2CF₃ | H | CH₃ | | |
| 14c | H | H | H | H | Cl | | |
| 21 | H | H | H | 5-OH | H | | 188–190 |
| 22c | H | H | H | 5-Cl | H | | 130–132 |

TABLE III $$R^1-N-\overset{\overset{O}{\|}}{C}-R^9$$

(indole ring with X substituent, $R^6$ at 2-position, Y at 3-position)

| Ex. | $R^1$ | $R^6$ | $R^9$ | X | Y | mp °C. |
|---|---|---|---|---|---|---|
| 1a | H | H | CH₂NHCO₂CH₂C₆H₅ | H | H | 144–148 |
| 2a | H | H | CH(CH₂OH)NHCO₂CH₂C₆H₅ | H | H | 124–127 |
| 3a | CH₂CO₂CH₂C₆H₅ | H | CH₂NHCO₂CH₂C₆H₅ | H | H | oil |
| 4a | H | H | CH₂NHCO₂CH₂C₆H₅ | H | CH₃ | 118–120 |
| 5a | CH₃ | H | CH₂NHCO₂CH₂C₆H₅ | H | H | 84–88 |
| 6a | H | H | CH₂NHCO₂C(CH₃)₃ | H | CH₃ | 142–145 |
| 6b | H | Cl | CH₂NHCO₂C(CH₃)₃ | H | CH₃ | 154-156 |
| 7b | H | H | CH₂NHCO₂CH₂C₆H₅ | 5-OCH₃ | H | 138–141 |
| 8b | H | H | CH₂NHCO₂CH₂C₆H₆ | 5-OCH₂C₆H₅ | H | 159–161 |
| 9c | H | (C=O)CH₃ | CH₂NHCO₂CH₂C₆H₅ | H | CH₃ | 153–155 |
| 10a | H | H | C₆H₄-2-COOH | H | CH₃ | 191–193 |
| 10e | H | (C=O)C₆H₄-2F | CH₂NHCO₂CH₂C₆H₅ | H | CH₃ | 226–228 |
| 11c | H | (C=O)C₆H₄-4F | CH₂NHCO₂CH₂C₆H₅ | H | CH₃ | |
| 12c | H | (C=O)C₆H₄-2CF₃ | CH₂NHCO₂CH₂C₆H₅ | H | CH₃ | |
| 13a | H | Br | CH₂NHCO₂CH₂C₆H₅ | H | CH₃ | 148–150 |
| 14b | H | H | CH₂NHCO₂C(CH₃)₃ | H | Cl | 156–158 |
| 15 | H | H | CH₂NHCO₂C(CH₃)₃ | H | H | 140–143 |
| 16 | H | Cl | CH₂NHCO₂CH₂C₆H₅ | H | CH₃ | 150–152 |
| 17 | H | H | CH₂NHCO₂C(CH₃)₃ | 5-OCH₂C₆H₅ | H | 115–119 |

TABLE III-continued $$R^1-N-\overset{\overset{O}{\|}}{C}-R^9$$

(structure: X-substituted indole with N-R6 and Y positions, with R1-N-C(=O)-R9 on indole nitrogen)

| Ex. | R¹ | R⁶ | R⁹ | X | Y | mp °C. |
|---|---|---|---|---|---|---|
| 18a | H | H | C(CH₃)₃ | H | CH₃ | 179–181 |
| 18b | H | CH(OH)C₆H₄-2F | C(CH₃)₃ | H | CH₃ | 152–155 |
| 19 | H | H | OC(CH₃)₃ | H | H | 112–116 |
| 20 | H | H | C₆H₄-2-CO₂H | H | H | 185–190 |
| 22b | H | H | CH₂NHCO₂C(CH₃)₃ | 5-Cl | H | 151–154 |
| 23 | H | (C=O)CH₃ | CH₂NHCO₂C(CH₃)₃ | H | CH₃ | 165–168 |
| 24 | H | H | CH₂N(CH₃)CO₂C(CH₃)₃ | H | H | 104–106 |
| 25 | H | H | (CH₂)₂NHCO₂C(CH₃)₃ | H | H | 138–140 |

TABLE IV (phthalimide-substituted indole structure with R⁶ and CH₃ substituents)

| Ex. | R⁶ | mp °C. |
|---|---|---|
| 9a | (C=O)CH₃ | 261–262 |
| 10b | H | 186–187 |
| 10c | (C=O)C₆H₄-2F | 197–199 |
| 11a | (C=O)C₆H₄-4F | 227–228 |
| 12a | (C=O)C₆H₄-2CF₃ | 203–205 |

TABLE V (N-amino indole structure with X, R⁶, and Y substituents)

| Ex. | R⁶ | X | Y | mp °C. |
|---|---|---|---|---|
| 7a | H | 5-OCH₃ | H | 115–117 |
| 8a | H | 5-OCH₂C₆H₅ | H | |
| 9b | (C=O)CH₃ | H | CH₃ | 94–98 |
| 10d | (C=O)C₆H₄-2F | H | CH₃ | |
| 11b | (C=O)C₆H₄-4F | H | CH₃ | |
| 12b | (C=O)C₆H₄-2CF₃ | H | CH₃ | |
| 14a | H | H | Cl | |
| 22a | H | 5-Cl | H | |

EXPERIMENTAL

EXAMPLE 1

[N-(1H-Indol-1-yl)-2-amino]acetamide hydrochloride a. [N-(1-Indol-1-yl)-2-(carbamic acid, phenylmethyl ester)]acetamide To a stirred suspension of 6.31 g of N-aminoindole, 120 ml of dry dichloromethane (DCM hereinafter) and 10.0 g of carbobenzyloxyglycine (CBZ glycine) was added 9.84 g of 1,3-dicyclohexylcarbodiimide (DCC). The mixture was stirred for 6 hours at room temperature. The suspension was filtered and the filtrate concentrated to a dark brown oil which was dissolved in DCM and flash chromatographed on silica gel, eluting with 60% DCM/hexane, DCM, 10% ethyl acetate/DCM and 15% ethyl acetate/DCM to provide 3.03 g of a tan solid. Recrystallization from ethyl acetate provided 2.06 g of analytically pure material, m.p. 140°–144° C. Concentration of the mother liquor afforded a solid which was triturated with hot ethyl acetate, filtered hot, allowed to cool to room temperature and filtered again. The resulting solution was treated with 1 g of activated carbon, concentrated from approximately 300 ml to approximately 200 ml, heated on a steam bath to dissolve any residual solid and allowed to stand overnight. Filtration provided an additional 4.18 g of the product, m.p. 140°–144° C., for a combined yield of 6.24 g.

ANALYSIS: Calculated for $C_{18}H_{17}N_3O_3$: 66.86% C 5.30% H 13.00% N Found: 66.66% C 5.08% H 12.88% N b. [N-(1H-Indol-1-yl)-2-amino]acetamide hydrochloride A suspension of 3.92 g of N-(1H-indol-1-yl)-2-(carbamic acid, phenylmethyl ester)acetamide, 0.8 g of 5% palladium on carbon and 200 ml of methanol was stirred under 1 atm of hydrogen for 12 minutes. The mixture was filtered and concentrated to an oil, which was dissolved in ethyl acetate and again filtered. To the filtrate at 0°–5° C. under nitrogen was added dropwise a solution of ethereal hydrogen chloride until precipitation was complete. The resulting suspension was allowed to warm to room temperature, filtered, washed with ethyl acetate and dried to provide 2.22 g of the product, m.p. 260°–262° C. (dec.).

ANALYSIS: Calculated for $C_{10}H_{12}ClN_3O$: 53.22% C 5.36% H 18.62% N Found: 53.10% C 5.35% H 18.34% N Alternatively N-(1H-indol-1-yl)-2-(amino)acetamide is prepared from the compound of Example 15 following substantially the procedure described in Example 6c.

EXAMPLE 2

[N-(1H-Indol-1-yl)-2-amino-2-(hydroxymethyl)] acetamide hydrochloride a. [N-(1H-Indol-1-yl)-2-(carbamic acid, phenylmethyl ester)-2-(hydroxymethyl)]-acetamide To a mixture of 83.5 of N-aminoindole, 20 g of D,L-carbobenzyloxyserine and 17.2 g of DCC was added 100 ml of dry tetrahydrofuran (THF). The mixture was stirred at room temperature for 8 hours and allowed to stand at 0°–5° C. overnight. The mixture was dissolved/suspended in chloroform, flash chromatographed on silica gel, eluting with chloroform followed by 20% ethyl acetate/chloroform to provide 7.8 g of N-[1H-indol-1-yl]-2-(carbamic acid, phenylmethyl ester)-2-(hydroxymethyl)acetamide. Recrystallization from chloroform/ethyl acetate provided a powder, m.p. 124°–127° C.

ANALYSIS: Calculated for $C_{19}H_{19}N_3O_4$: 64.58% C 5.42% H 11.89% N Found: 64.71% C 5.42% H 11.95% N b. [N-(1H-Indol-1-yl)-2-amino-2-(hydroxymethyl)] acetamide hydrochloride A suspension of 1.0 g of 5% palladium on carbon, 250 ml of methanol and 4.7 g of Example 2a was stirred under 1 atmosphere of hydrogen for one hour. The suspension was filtered and the filtrate poured into a second reaction flask containing 1 g of 5% palladium on carbon. This suspension was stirred under a hydrogen atmosphere for one hour, filtered and concentrated in vacuo to an oil, which was dissolved in ethyl acetate and filtered to remove some insoluble material. The filtrate was cooled in an ice bath under a dry nitrogen atomosphere and ethereal hydrogen chloride (HCl) was added. The resulting precipitate was allowed to settle and the solid triturated with ether, allowed to warm to room temperature and filtered. The dried solid (2.51 g) was recrystallized from ethanol to yield 1.58 g of N-(1H-indol-1-yl)-2-amino-2-(hydroxymethyl)acetamide hydrochloride, m.p. 216°–220° C.

ANALYSIS: Calculated for $C_{11}H_{14}ClN_3O_2$: 51.67% C 5.52% H 16.43% N Found: 51.71% C 5.56%h 16.31% N

EXAMPLE 3

[[N-(1H-Indol-1-yl)-2-amino]acetamide]acetic acid a. [[N-(1H-Indol-1-yl)-2-(carbamic acid, phenylmethyl ester)]acetamide]acetic acid, phenylmethyl ester A suspension of 9.3 g of Example 1a, 20 ml of acetonitrile, 10.4 g of 40% KF on alumina (neutral, 100–125 mesh, dried one hour at 80° C. (2 mm)) and 5.47 ml (7.93 g) of benzyl 2-bromoacetate was stirred at room temperature for 12 hours. To the suspension was added an additional 1 ml of benzyl 2-bromoacetate. The suspension was stirred for 12 hours, filtered and concentrated to an oil. The oil was dissolved in ethyl acetate and flash chromatographed on silica gel, eluting with 30% ethyl acetate/hexanes to yield 12.3 g of the desired product as an oil.

ANALYSIS: Calculated for $C_{27}H_{25}N_3O_5$: 68.78% C 5.34% H 8.91% N Found: 69.09% C 5.56% H 8.59% N b. [[N-(1H-Indol-1-yl)-2-amino]acetamide]acetic acid A suspension of 8.0 g of Example 3a, 2 L of methanol and 1.5 g of 5% palladium on carbon was stirred at room temperature under 1 atm of $H_2$ for one hour. The suspension was filtered and the filtrate concentrated to provide a white suspension (~300 ml). The suspension was filtered and the residue dried to provide 2.35 g of [[N -(1H-indol-1-yl)-2-amino]acetamide]acetic acid, m.p. 197°–200° C. Recrystallization from methanol/water raised the m.p. to 212°–216° C. The filtrate from above was concentrated to provide an additional 0.52 g for a total yield of 2.87 g.

ANALYSIS: Calculated for $C_{12}H_{13}N_3O_3$: 58.29% C 5.30% H 16.99% N Found: 57.99% C 5.19% H 16.75% N

EXAMPLE 4

[N-(3-Methyl-1H-indol-1-yl)-2-amino]acetamide hydrochloride a. [[N-(3-Methyl-1H-indol-1-yl)]-2-(carbamic acid, phenylmethyl ester)]acetamide A suspension of 13.9 g of 3-methyl-N-aminoindole, 240 ml of dry DCM and 20 g of DCC was stirred at room temperature overnight. The suspension was filtered, and the filtrate concentrated and the residual oil flash chromatographed on silica gel, eluting with dichloromethane, 10% ethyl acetate/dichloromethane and 20% ethyl acetate/dichloromethane, to provide 22.9 g of product. The product was dissolved in chloroform and flash chromatographed on silica gel, eluting with chloroform and 10% ethyl acetate/chloroform to provide pure N-(3-methyl-1H-indol-1-yl)-2-(carbamic acid, phenylmethyl ester)acetamide, m.p. 118°–120° C.

ANALYSIS: Calculated for $C_{19}H_{19}N_3O_3$: 67.64% C 5.68% H 12.45% N Found: 67.34% C 5.63% H 12.36% N b. [N-(3-Methyl-1H-indol-1-yl)-2-amino]acetamide hydrochloride To a suspension of 0.6 g of 5% Pd on carbon and 90 ml of methanol was added, under nitrogen, a solution of 3.0 g of Example 4a in 60 ml of dry methanol. The suspension was stirred under 1 atm of hydrogen for 45 minutes, filtered and the filtrate concentrated to an oil. The oil was treated with anhydrous ether and the mixture decanted. The supernatant was concentrated to an oil which was dissolved in ethyl acetate and the resulting solution, under nitrogen, cooled in an ice bath. To the stirred solution was added ethereal HCl until precipitation ceased and the suspension was acidic. To the suspension was then added anhydrous ether, after which it was stirred 5 minutes and allowed to warm to room temperature. The suspension was filtered, and the residue was washed with ether and dried to provide 1.21 g of [N-(3-methyl-1H-indol-1-yl)-2-amino]acetamide hydrochloride, m.p. 260°–270° C. (dec.).

ANALYSIS: Calculated for $C_{11}H_{14}ClN_3O$: 55.12% C 5.89% H 17.53% N Found: 55.01% C 5.86% H 17.20% N Alternatively, [N-(3-methyl-1H-indol-1-yl)-2-amino] acetamide hydrochloride is prepared from the compound of Example 6a following substantially the procedure described in Example 6c.

EXAMPLE 5

[N-(Methyl)-N-(1H-indol-1-yl)-2-amino]acetamide hydrochloride a. [[N-(Methyl)-N-(1H-indol-1-yl)]-2-(carbamic acid, phenylmethyl ester)]acetamide To a stirred suspension of 9.0 g of Example 1a in 20 ml of acetonitrile was added 9.9 g of 40% KF on alumina (dried 4–5 hours at 75°–80° C., 2 mm) after which was added 2.07 ml (4.72 g) of iodomethane. The suspension was stirred at room temperature for 20 hours. The reaction mixture was diluted with acetonitrile, filtered and the filtrate concentrated to an oil. The oil was flash chromatographed on silica gel, eluting with chloroform followed by 5% ethyl acetate/chloroform, to provide 9.6 g of an oil which crystallized on standing for several days to give 7.3 g of [[N-(methyl)-N-

(1H-indol-1-yl)]-2-(carbamic acid, phenylmethyl ester)] acetamide, m.p. 84°–88° C.

ANALYSIS: Calculated for $C_{19}H_{19}N_3O_3$: 67.64% C 5.68% H 12.45% N Found: 67.71% C 5.63% H 12.45% N b. [(N-(Methyl)-N-(1H-indol-1-yl)-2-amino]acetamide hydrochloride A solution of 4.60 g of Example 5a dissolved in 100ml of dry methanol was added to a suspension of 0.5 g of 5% palladium on carbon in 130 ml of dry methanol. The mixture was stirred at room temperature under 1 atm of hydrogen for 1.75 hours. The suspension was filtered and the filtrate concentrated to an oil which was dissolved in ether and filtered. To the filtrate was added ethereal HCl until precipitation ceased. The suspension was filtered and the residue washed with ether and dried at room temperature in vacuo (2 mm Hg). The white solid (1.92 g) was recrystallized from 100% ethanol to provide 1.67 g of [(N-methyl)-N-(1H-indol-1-yl)-2-amino]acetamide hydrochloride, m.p. 253°–258° C. (dec.).

ANALYSIS: Calculated for $C_{11}H_{14}ClN_3O$: 55.12% C 5.89% H 17.53% N Found: 55.05% C 5.93% H 17.32% N

EXAMPLE 6

[N-(2-Chloro-3-methyl-1H-indol-1-yl)-2-amino] acetamide hydrochloride a. [[N-(3-Methyl-1H-indol-1-yl)]-2-(carbamic acid, t-butyl ester)]acetamide To a stirred solution of 15 g of N-amino-3-methylindole, 18.0 g of t-butyoxycarbonylglycine and 250 ml of dry DCM was added 21.2 g of DCC. The mixture was stirred for 3.5 hours at room temperature, filtered and the filtrate concentrated to provide an off-white solid. The material was purified by flash chromatography on silica gel, eluting with 10% ethyl acetate/dichloromethane followed by 15% ethyl acetate/dichloromethane to provide 25.4 g of [[N-(3-methyl-1H-indol-1-yl)]-2-(carbamic acid, t-butyl ester)]acetamide, m.p. 142°–145° C.

ANALYSIS: Calculated for $C_{16}H_{21}N_3O_3$: 63.35% C 6.98% H 13.85% N Found: 63.42% C 6.86% H 13.59% N b. [[N-(2-Chloro-3-methyl-1H-indol-1-yl)]-2-(carbamic acid, t-butyl ester)]acetamide To a stirred solution of 10.0 g of Example 6a, 3.96 g of N-chlorosuccinimide and 350 ml of dry dimethylformamide (DMF hereinafter) was added 50 mg of 2,2'-azobis(2-methylpropionitrile) (AIBN). The solution was stirred for 10 minutes at room temperature and 1 hour at 40° C. The solution was allowed to cool to room temperature; diluted with ethyl acetate; washed with water, brine, dried ($Na_2SO_4$), filtered and concentrated to an oil. The oil was dissolved in chloroform and purified by HPLC (silica), eluting with chloroform to provide 6.34 g of [[N-(2-chloro-3-methyl-1H-indol-1-yl)]-2-(carbamic acid, t-butyl ester)] acetamide, m.p. 154°–156° C.

ANALYSIS: Calculated for $C_{16}H_{20}ClN_3O_3$: 56.89% C 5.97% H 12.44% N Found: 56.94% C 5.86% H 12.29% N c. [N-(2-Chloro-3-methyl-1H-indol-1-yl)-2-amino] acetamide hydrochloride To a stirred solution of 3.5 g of [[N-(2-chloro-3-methyl-1H-indol-1-yl)]-2-carbamic acid, t-butyl ester]acetamide in 44 ml of dry ethyl acetate in an ice bath under nitrogen was added a solution of 87 ml of 1M HCl in ethyl acetate. The mixture was allowed to warm to room temperature and stirred for 18 hours. The resulting suspension was filtered and the filtrate washed with ethyl acetate and subsequently dried at 80° C. in vacuo (2 mm Hg) to provide 2.51 g of [N-(2-chloro-3-methyl-1H-indol-1-yl)-2-amino]acetamide hydrochloride, m.p. 248°–249° C. (dec.).

ANALYSIS: Calculated for $C_{11}H_{13}Cl_2N_3O$: 48.19% C 4.78% H 15.33% N Found: 47.88% C 4.67% H 15.09% N The compounds of Example 22b and c (Tables III & II, respectively) were prepared from N-amino-5-chloroindole following substantially the process set forth in parts a and c in this example.

EXAMPLE 7

[N-(5-Methoxy-1H-indol-1-yl)-2-amino]acetamide a. N-(Amino)-5-(methoxy)-1H-indole 5-Methoxyindole (15.0 g) was dissolved in anhydrous DMF (90 ml), cooled to 0° C., and milled KOH (28 g) was added. Upon completion of addition, hydroxylamine-O-sulfonic acid (14.7 g) was added portionwise over a period of 1 hour. The reaction temperature was maintained below 20° C. during this addition. The mixture was stirred at 0° C. for 1 hour and then poured into 200 ml of water ($H_2O$). The product was extracted into dichloromethane and washed with brine (2×100 ml). The organic phase was dried ($Na_2SO_4$), filtered and concentrated to a deep red oil. This material was purified using preparative HPLC (silica), eluting with 30% hexane in ethyl acetate to yield a solid, m.p. 115°–117° C.

ANALYSIS: Calculated for $C_9H_{10}N_2O$: 66.65% C 6.21% H 17.27% N Found: 66.37% C 6.18% H 17.14% N N-amino-5-chloroindole was prepared from 5-chloroindole following substantially the process set forth in this example.

b. [N-(5-Methoxy-1H-indol-1-yl)-2-(carbamic acid, phenylmethyl ester)]acetamide

N-Carbobenzyloxyglycine (4.80 g) was dissolved in anhydrous dioxane (80 ml) and treated with 1-hydroxybenzotriazole (3.10 g) at room temperature under $N_2$. The mixture was cooled to 0° C. and treated with solid 1-amino-5-methoxy-1H-indole (3.71 g) followed by DCC (4.7 g). The mixture was allowed to slowly warm to room temperature and stirred for 48 hours. The solvent was removed in vacuo and the residue was triturated with dichloromethane. The insoluble material was collected by filtration and recrystallized from ethanol. The filtrate from the crude reaction mixture was diluted with dichloromethane (100 ml), washed with brine (1×100 ml), saturated $NaHCO_3$ (1×100 ml), brine (1×50 ml) and dried ($Na_2SO_4$). Upon filtration and evaporation of the solvent, the residue was chromatographed on silica gel. The powder was applied to silica gel to yield N-(5-methoxy)-1H-indol-1-yl)-2-(carbamic acid, phenylmethyl ester)acetamide, m.p. 138°–141° C.

ANALYSIS: Calculated for $C_{19}H_{19}N_3O_4$: 64.58% C 5.42% H 11.89% N Found: 64.66% C 5.54% H 11.76% N c. [N-(5-Methoxy-1H-indol-1-yl)-2-amino]acetamide

[N-(5-Methoxy-1H-indol-1-yl)-2-amino]acetamide is prepared from Example 7b following substantially the procedure set forth in Example 1b.

EXAMPLE 8

[N-(5-Phenylmethoxy-1H-indol-1-yl)-2-amino] acetamide a. N-Amino-5-phenylmethoxy-1H-indole N-Amino-5-phenylmethoxy-1H-indole was prepared from 5-phenylmethoxyindole using substantially the procedure described in Example 7a.

b. [N-(5-Phenylmethoxy-1H-indol-1-yl)-2-(carbamic acid, phenylmethyl ester)]acetamide N-Carbobenzyloxyglycine (1.93 g) was dissolved in dry dioxane (23 ml) and treated with 1-hydroxybenzothiazole (1.24 g). The mixture was then cooled to 0° C. and DCC (1.73 g) and N-amino-5-phenylmethoxy-1H-indole (2.0 g) were added sequentially. The solution was stirred at room temperature under $N_2$ for 48 hours. The dioxane was removed under reduced pressure and the solid residue was dissolved in DCM. The insoluble material was removed by filtration and recrystallized from ethanol to yield a small amount of the product. The filtrate was purified using preparative HPLC (silica), eluting with heptane/EtOAc (1:1), to yield a solid which was recrystallized from ethanol, m.p. 159°–161° C.

ANALYSIS: Calculated for $C_{25}H_{23}N_3O_4$: 69.92% C 5.40% H 1 9.78% N Found: 69.93% C 5.31% H 9.80% N c. [N-(5-Phenylmethoxy-1H-indol-1-yl)-2-amino]acetamide The compound of Example 8b was dissolved in 75 ml of methanol. The solution at room temperature was added to 0.1 g of 10% Pd on C. The suspension was stirred under 1 atm of hydrogen for ½ hour. The suspension was filtered and concentrated to an oil. The oil was treated with ethyl acetate after which a solid was obtained. The solid was removed by filtration and dried. The filtrate was concentrated to provide an oil which was dissolved in 10% methanol/$CHCl_3$ and allowed to stand for 2 hours. A crystalline solid was isolated by filtration. The filtrate was purified by flash chromatography on silica gel, eluting with 10% methanol/chloroform followed by 20% methanol/chloroform to yield an oil which was dissolved in ethyl acetate/ether and the hydrochloride salt precipitated by addition of ethereal hydrogen chloride. The white solid was isolated by filtration, dried and recrystallized from ethanol to provide analytically pure material, m.p. 146–150 d.

ANALYSIS: Calculated for: $C_{17}H_{18}ClN_3O_2$: 61.54% C 5.47% H 12.66% N Found: 61.65% C 5.28% H 12.61% N

EXAMPLE 9

[N-(2-Acetyl-3-methyl-1-indol-1-yl)-2-amino]acetamide a. 2-(2-Acetyl-3-methyl-1H-indol-1-yl)-1H-isoindole-1,3-(2H)dione 2-(2-acetyl-3-methyl-1H-indol-1-yl)-1H-isoindole-1,3-(2H)dione was prepared from Compound 10b and acetyl chloride following substantially the procedure described in Example 10c.

b. 2-Acetyl-1-amino-3-methyl-1H-indole

To the 10.5 g of 2-(2-acetyl-3-methyl-1H-indol-1-yl)-1H-isoindole-1,3-(2H)dione under nitrogen was added 52.0 ml of degassed dimethylformamide followed by 52.0 ml of degassed 40% aqueous methylamine. The solution was stirred at room temperature under nitrogen for 2 hours, poured onto ice/water/ethyl acetate, extracted three times with ethyl acetate, washed with water, brine, dried over sodium sulfate, filtered and concentrated to an oil weighing 6.93 g. Chromatographic purification, eluting with chloroform gave 5.60 g of a solid. Recrystallization using isopropyl alcohol, gave 2.50 g of 2-acetyl-1-amino-3-methyl-1H-indole, m.p. 94°–98° C.

ANALYSIS: Calculated for $C_{11}H_{12}N_2O$: 70.19% C 6.43% H 14.88% N Found: 69.82% C 6.34% H 14.68% N c. [N-(2-Acetyl)-3-methyl-(1H-indol-1-yl)]-2-(carbamic acid, phenylmethyl ester)]acetamide

[N-(2-Acetyl)-3-methyl-(1H-indol-1-yl)]-2-(carbamic acid, phenylmethyl ester)]acetamide was prepared from the compound of Example 9b using substantially the process described in Example 1a to yield the desired product, m.p. 153°–155° C.

ANALYSIS: Calculated for: 66.48% C 5.58% H 11.07% N Found: 66.26% C 5.73% H 10.85% N d. [N-(2-Acetyl-3-methyl-1H-indol-1-yl)-2-amino] acetamide [N-(2-Acetyl-3-methyl-1H-indol-1-yl)-2-amino] acetamide is prepared from Example 9c using substantially the process described in Example 1b.

EXAMPLE 10

[N-[2-(2-Fluorobenzoyl)-3-methyl-1H-indol-1-yl]-2-amino]acetamide a. 2-[[(3-Methyl-1H-indol-1-yl)amino]carbonyl]benzoic acid A suspension of 2.0 g of N-amino-3-methylindole, 140 ml of dry chloroform and 2.74 g of phthalic anhydride was stirred at reflux for 4 hours. The suspension was allowed to cool to room temperature, concentrated to approximately 50 ml, filtered and the residue washed with chloroform to provide 4.25 g of a white solid. Recrystallization from ethyl acetate provided 3.18 g (79.0%) of 2-[[(3-methyl(indol-1-yl)amino]carbonyl]benzoic acid, m.p. 191°–193° C.

The compound of Example 20 (Table III) is prepared from N-aminoindole following substantially the same process.

b. 2-[3-Methyl-1H-indol-1-yl-1H-isoindole-1,3-(2H)dione

A suspension of 14.0 g of Example 14a, 10.7 g of DCC, 140 ml of dry $CHCl_3$ and 560 mg of dimethylaminopyridine was stirred at room temperature under nitrogen for 14 hours. The suspension was filtered, the filter cake washed with a small volume of chloroform, the filtrate concentrated to about 50 ml and flash chromatographed on silica gel, eluting with dichloromethane to provide 11.6 g of 2-[3-(methyl-1H-indol-1-yl]1H-isoindole-1,3-(2H)dione, m.p. 186°–187° C.

ANALYSIS: Calculated for $C_{17}H_{14}N_2O_3$: 73.90% C 4.38% H 10.14% N Found: 73.83% C 4.33% H 10.07% N c. 2-[2-(2-Fluorobenzoyl)-3-methyl-1H-indol-1-yl]-1H-isoindole-1,3-(2H)dione A solution of 0.91 ml of 2-fluorobenzoyl chloride in 50 ml of dry DCM was cooled in an ice/salt bath. To the solution was added 0.86 ml (1.91 g) of tin (IV) chloride. The mixture was stirred at –5° to 0° C. for 10 minutes after which was added 2.0 g of 2-(3-methyl-1H-indol-1-yl)-1H-isoindole-1,3-(2H)dione. The reaction mixture was stirred at 0° C. for 1 hour, allowed to warm to room temperature, cooled again in an ice bath, poured onto ice, extracted twice with ethyl acetate, washed with water, brine, dried ($Na_2SO_4$), filtered and concentrated to a green-yellow solid (2.67 g). The solid was chromatographed on silica gel, eluting with 15% acetone/heptane to provide 1.99 g of a solid, which was recrystallized from ethanol, m.p. 197°–199° C.

ANALYSIS: Calculated for $C_{24}H_{15}FN_2O_3$: 72.36% C 3.80% H 7.03% N Found: 72.03% C 3.92% H 7.01% N d. N-Amino-2-(2-fluorobenzoyl)-3-methyl-1H-indole To 10.2 g of Example 10c under nitrogen was added 50 ml of degassed DMF, followed by 50 ml of degassed 40% aqueous methylamine. The solution was stirred at room temperature under nitrogen for 3 hours, poured onto ice/water/ethyl acetate, extracted 3× with ethyl acetate, washed with water, brine, dried, filtered and concentrated to yield a brown solid. The solid material was dissolved in a minimum volume of ethyl acetate and purified by HPLC (silica) to provide 5.82 g of a brown solid.

e. [N-[2-(2-Fluorobenzoyl)-3-methyl-1H-indol-1-yl]-2-(carbamic acid, phenylmethyl ester)]acetamide A suspension of 1.00 g of Example 10d, 15 ml of dry DCM, 0.78 g of CBZ glycine and 0.78 g of DCC was stirred at room temperature under nitrogen for 6 hours. The suspension was filtered, the filter cake washed with dry DCM, and the combined filtrate concentrated to an oil. The oil was dissolved in ethyl acetate and purified by flash chromatography on silica gel, eluting with ethyl acetate/heptane (10%, 15%, 20% and 25%, respectively) to provide 0.84 g of a yellow oil which crystallized on standing, m.p. 226°–228° C.

ANALYSIS: Calculated for $C_{26}H_{22}FN_8O_4$: 67.97% C 4.83% H 9.15% N Found: 68.00% C 4.90% H 9.07% N f. [N-[2-(2-Fluorobenzoyl)-3-methyl-1H-indol-1-yl]-2-amino]acetamide A suspension of 5.0 g of Example 10e, 620 ml of dry methanol and 1.0 g of 10% Pd/C was stirred under 1 atm of hydrogen for 5 hours. The suspension was filtered and the filtrate was concentrated to an oil. The oil was dissolved in 5% methanol/dichloromethane and flash chromatographed on silica gel, eluting with the same solvent mixture to yield an oil. The oil was dissolved in a minimum volume of ethyl acetate, diluted with ether and the hydrochloride precipitated by addition of ethereal HCl to provide 2.14 g of a yellow solid, m.p. 150°–170° C.

ANALYSIS: Calculated for $C_{18}H_{16}FN_3O_2 \cdot HCl$: 59.76% C 4.74% H 11.61% N Found: 59.60% C 4.77% H 11.51% N

EXAMPLE 11

[N-[2-(4-Fluorobenzoyl)-3-methyl-1H-indol-1-yl]-amino]acetamide hydrochloride a. 2-[2-(4-Fluorobenzoyl)-3-methyl-1H-indol-1-yl]-1H-isoindole-1,3-(2H)dione A solution of 8.14 ml of 4-fluorobenzoyl chloride and 450 ml of dry DCM was cooled in an ice/salt bath to 0° C. To the stirred solution was added 7.74 ml of tin (IV) chloride. The mixture was stirred at –5° C. to 0° C. for 10 minutes after which was added 18.0 g of 2-[(3-methyl-1H-indol-1-yl]-1H-isoindole-1,3-(2H)dione (Example 10b). The reaction mixture was stirred at 0° C. for 1.5 hours, allowed to warm to room temperature for 2 hours, cooled again in an ice bath, poured onto ice, extracted twice with ethyl acetate, washed with water, brine, dried over sodium sulfate, filtered and concentrated to a yellow solid. Chromatography (15% acetone/heptane) provided a solid weighing 56.8 g. Recrystallization from ethyl alcohol gave 21.1 g of the product, m.p. 227°–228° C.

ANALYSIS: Calculated for: $C_{24}H_{15}FN_2O_3$: 72.36% C 3.80% H 7.03% N Found: 72.45% C 3.82% H 6.93% N b. N-Amino-2-(4-fluorobenzoyl)-3-methyl-1H-indole N-amino-2-(4-fluorobenzoyl)-3-methyl-1H-indole was prepared from Compound 11a using substantially the procedure described in Example 10d.

c. [N-[2-(4-Fluorobenzoyl)-3-methyl-1H-indol-1-yl]-2-(carbamic acid, phenylmethyl ester)]acetamide

[N-[2-(4-Fluoro)benzoyl)-3-methyl-1H-indol-1-yl]-2-carbamic acid phenylmethyl ester acetamide was prepared from the Compound 11b using substantially the procedure described in Example 10e.

d. [N-[2-(4-Fluorobenzoyl)-3-methyl-1H-indol-1-yl)]-2-amino]acetamide.

A suspension of 5.41 g of [N-[2-(4-fluorobenzoyl)-3-methyl-1H-indol-1-yl)]-2-(carbamic acid, phenylmethyl ester)]acetamide, 670 ml of dry methanol and 1.08 g of 10% Pd on carbon was stirred under 1 atm of hydrogen for 45 minutes. The suspension was filtered and the filtrate concentrated to a solid weighing 3.71 g. The solid was dissolved in minimal volume of DCM, and chromatographed on silica, eluting with chloroform and 5% methanol:chloroform. Fractions containing the product were concentrated to give 2.48 g of a solid. The solid was dissolved in minimal volume of ethyl acetate, diluted with ethyl ether and ethereal hydrogen chloride was added. The resulting solid was collected and dried for 2 hours to yield 2.06 g of the product, m.p. 160°–170° C.

EXAMPLE 12

[N-[2-[2-(Trifluoromethyl)benzoyl]-3-methyl-1 1H-indol-1-yl]-2-amino]acetamide a. 2-[2-[2-(Trifluoromethyl)benzoyl]-3-methyl-1H-indol-1-yl]-1H-isoindole-1,3-(2H)dione To a stirred solution of 1.59 g of 2-(trifluoromethyl)benzoyl chloride in 50 ml of dry DCM at 5° C. was added 0.86 ml (1.92 g) of tin IV chloride. The solution was stirred at –5° C. for 10 minutes. To the solution was added 2.0 g of 2-[(3-methyl-1H-indol-1-yl]-1H-isoindole-1,3-(2H)dione. The solution was stirred for 2 hours at 5° C. and poured onto ice/water/ethyl acetate. The mixture was extracted with ethyl acetate, washed with water, brine, dried, filtered and concentrated to a white solid. The material was purified by HPLC (silica), eluting with 10% acetone/heptane, 15% acetone/heptane and ethyl acetate to provide 2.27 g of 2-[2-(2-trifluoromethyl)benzoyl-3-methyl-1H-indol-1-yl]-1H-isoindole-1,3-(2H)dione, m.p. 202°–205° C.

b. N-Amino-2-[2-(trifluoromethyl)benzoyl]-3-methyl-1H-indole

N-Amino-2-(2-(trifluoromethyl)benzoyl)-3-methyl-1H-indole is prepared from Example 12a using substantially the procedure described in 10d.

c. [N-[2-[2-(Trifluoromethyl)benzoyl]-3-methyl-1H-indol-1-yl]-2-(carbamic acid, phenylmethyl ester)]acetamide

[N-[2-[2-(Trifluoromethyl)benzoyl]-3-methyl-1H-indol-1-yl]-2-(carbamic acid phenylmethyl ester)]acetamide is prepared from Example 12b using substantially the procedure described in Example 10e.

d. [N-[2-[2-(Trifluoromethyl)benzoyl]-3-methyl-1H-indol-1-yl]-2-amino]acetamide

[N-[2-[2-Trifluoromethyl)benzoyl]-3-methyl-1H-indol-1-yl]-2-amino]acetamide is prepared from Example 12c using substantially the procedure described in Example 10f.

EXAMPLE 13

[[N-(2-Bromo-3-methyl-1H-indol-1-yl)]-2-(carbamic acid, phenylmethyl ester)]acetamide To 3 g of [[N-(3-methyl-1H-indol-1-yl)]-2-(carbamic acid, phenylmethyl ester)]acetamide Example 4a and 1.59 g of N-bromosuccinamide was added 75 ml of dry DMF. The mixture was stirred at room temperature for 10 minutes and at 40° C. for 3 hours. The solution was allowed to cool to room temperature, diluted with ethyl acetate, poured onto ice, washed twice with water, once with brine, dried ($Na_2SO_4$), filtered and concentrated to an oil. The material was dissolved in chloroform and flash chromatographed on silica gel, eluting with chloroform followed by 1% ethyl acetate/chloroform to provide 2.29 g of [[N-(2-bromo-3-methyl-1H-indol-1-yl)]-2-(carbamic acid, phenylmethyl ester)]acetamide, m.p. 148°–150° C.

ANALYSIS: Calculated for $C_{19}H_{18}BrN_3O_3$: 54.82% C 4.36% H 10.09% N Found: 55.21% C 4.36% H 10.02% N

EXAMPLE 14

[N-(3-Chloro)-1H-indol-1-yl)-2-amino]acetamide a. N-Amino-3-chloro-1H-indole

To a stirred solution of 12.6 g of 3-chloroindole in 125 ml of dry DMF at 0° C. was added 0.5 g of milled $K_2CO_3$ in 20 ml of dry DMF, followed by 30 g of KOH in 20 ml of dry DMF. The mixture was cooled to about 0° C. after which was added 13.3 g of $NH_2OSO_3H$ such that the temperature did not rise above 0° C. When addition was complete, a second charge of 2.22 g of $NH_2OSO_3H$ was added. When addition was complete a third 2.22 g charge of $NH_2OSO_3H$ was added. The mixture was poured into ice/water/toluene, extracted into toluene, washed with water and concentrated to provide 5.6 g of an oil which crystallized on standing overnight.

b. [[N-(3-Chloro-1H-indol-1-yl]-2-(carbamic acid, t-butyl ester)]acetamide

To a stirred mixture of 2.0 g of 3-chloro-N-aminoindole, 2.14 g of t-BOC glycine and 30 ml of dry DCM was added 2.52 g of DCC. The mixture was stirred at room temperature, under nitrogen, for 18 hours. The suspension was filtered and the filtrate concentrated to an oil which was purified by HPLC on silica gel, eluting with DCM followed by 5% and 10% ethyl acetate/DCM, respectively to provide 1.01 g of product. The product was stirred in warm $CHCl_3$, allowed to cool to room temperature, filtered and purified by HPLC on silica to provide an additional 0.58 g of product for a total yield of 1.16 g of [[N-(3-chloro-1H-indol-1-yl)]-2-(carbamic acid, t-butyl ester)]acetamide, m.p. 156°–158° C.

ANALYSIS: Calculated for $C_{15}H_{18}ClN_3O_3$: 55.64% C 5.60% H 12.98% N Found: 56.03% C 5.68% H 12.85% N c. [N-(3-Chloro-1H-indol-1-yl)-2-amino]acetamide

[N-(3-Chloro-1H-indol-1-yl)-2-amino]acetamide is prepared using substantially the procedure described in Example 6c.

EXAMPLE 15

N-(1H-Indol-1-yl)-2-(carbamic acid, t-butyl ester) acetamide

To a stirred solution of 3.77 g of N-aminoindole, 5.0 g of t-butoxycarbonyl (t-BOC) glycine and 70 ml of dry DCM was added 5.89 g of DCC. The mixture was stirred for 2 hours at room temperature, filtered and concentrated to an oil which was purified by flash chromatography on silica gel, eluting with 30% ethyl acetate/hexanes. The product-containing fractions were combined, concentrated and flashed chromatographed on silica gel, eluting with 1:1 DCM/hexanes followed by 60% DCM/hexanes. The product-containing fractions were combined and concentrated to an oil which crystallized on standing to provide after drying at 80° C. (1 mm Hg) 4.70 g of [N-(1H-indol-1-yl)-2-(carbamic acid, t-butyl ester)]acetamide, m.p. 134°–138° C. Recrystallization from cyclohexane/ethyl acetate raised the m.p. to 140°–143° C.

ANALYSIS: Calculated for $C_{15}H_{19}N_3O_3$: 62.27% C 6.62% H 14.52% N Found: 61.90% C 6.53% H 14.32% N The compound of Example 23 (Table III) was prepared following substantially the process described in this example starting with the compound of Example 9b.

The compounds of Examples 24 and 25 (Table III) were prepared following substantially the process described in this example starting with N-aminoindole and N-(t-butoxycarbonyl)sarcosine and 3-(t-butoxy carbonylamino) propionic acid respectively and eluting DCM/ethyl acetate.

EXAMPLE 16

[[N-(2-Chloro-3-methyl-1H-indol-1-yl)]-2-(carbamic acid, phenylmethyl ester)]acetamide To a mixture of 10.0 g of Example 4a, 3.96 g of N-chlorosuccinimide and 50 mg of 2,2'-azobis(2-methylpropionitrile) (AIBN) was added, under nitrogen, 250 ml of DMF. The mixture was stirred for 15 minutes at room temperature, heated to 40° C. and stirred at that temperature for one hour. The mixture was allowed to cool to room temperature, diluted with ethyl acetate and extracted twice with ethyl acetate. The combined organic fractions were washed with water, brine, dried and concentrated to an oil. The oil was dissolved in chloroform and purified by flash chromatography on silica gel, eluting with chloroform followed by 2% ethyl acetate/chloroform to provide 8.02 g of product, m.p. 150°–152° C.

ANALYSIS: Calculated for $C_{19}H_{18}ClN_3O_3$: 61.38% C 4.88% H 11.30% N Found: 61.32% C 4.88% H 11.29% N

EXAMPLE 17

[N-(5-Phenylmethoxy-1H-indol-1-yl)-2-(carbamic acid, t-butyl ester)]acetamide

N-(tert-Butoxycarbonyl)glycine (0.740 g) was dissolved in anhydrous DCM (8.0 ml) and treated with 1-hydroxybenzotriazole hydrate (0.623 g) under a nitrogen atomosphere at room temperature. The resultant slurry was cooled to 0° C. and treated with DCC (0.95 g). After stirring for twenty minutes at this temperature, a solution of 1-amino-5-phenylmethoxy-1H-indole (Example 8a) (1.0 g) in DCM (2.0 ml) was added via cannula. The resulting mixture was allowed to gradually warm to room temperature and stirred for 20 hours. The mixture was extracted several times with brine, saturated $NaHCO_3$ (aq) and brine once again. The organic phase was dried ($Na_2SO_4$), filtered and concentrated to a tan powder. This material was dissolved in DCM and chromatographed on silica gel (hexane/EtOAc, 1:1) to afford 1.0 g of the product.

ANALYSIS: Calculated for $C_{22}H_{25}N_3O_4$: 66.82% C 6.37% H 10.63% N Found: 66.96% C 6.53% H 10.62% N

EXAMPLE 18

[2-[(2-Fluorophenyl)hydroxymethyl]-3-methyl-N-[(trimethylacetyl)amino]]-1H-indole a. [3-Methyl-N-[(trimethylacetyl)amino]]-1H-indole To a stirred solution of 2.0 g of 3-methyl-N-amino-1H-indole, 20 ml of dry DCM and 1.73 g (2.38 ml) of triethylamine in an ice bath was added dropwise a solution of 1.82 g (1.86 ml) of trimethylacetylchloride in 3 ml of DCM. The mixture was stirred at 0°–5° C. for 10–15 minutes, allowed to warm to room temperature and stirred for 2 hours at room temperature. The mixture was again cooled in an ice bath, poured into ice/water/ethyl acetate, extracted with ethyl acetate, washed with brine, dried ($Na_2SO_4$), filtered and concentrated to an oil which crystallized on standing. The material was purified by flash chromatography on silica gel, eluting with 2% and 5% ethyl acetate/DCM to provide 2.50 g of [3-methyl-N-[(trimethylacetyl)amino]]-1H-indole, m.p. 179°–181° C.

ANALYSIS: Calculated for $C_{14}H_{18}N_2O$: 73.01% C 7.88% H 12.16% N Found: 73.22% C 7.94% 12.14% N b. [2-[(2-Fluorophenyl)hydroxymethyl]-3-methyl-N-[(trimethylacetyl)amino]]-1H-indole To a stirred solution of 6.91 g of [3-methyl-N-[(trimethylacetyl)amino]]-1H-indole in 140 ml of dry tetrahydrofuran (THF) at −60° to −70° C. was added 53.5 ml of 1.2M nBuLi in hexanes. The mixture was allowed to warm to 0° C. and stirred for 45 minutes under nitrogen at 0° C. To the solution was added 4.73 ml (5.56 g) of 2-fluorobenzaldehyde. The mixture was stirred for several minutes at 0° C., allowed to warm to room temperature and again cooled in an ice bath. The mixture was poured into ice/water, extracted twice with ethyl acetate, washed with water, brine, dried ($Na_2SO_4$), filtered and concentrated to an oil which crystallized on standing. The material was purified by HPLC on silica gel to provide 10.6 g of [2-[(2-fluorophenyl)hydroxymethyl]-3-methyl-N-[(trimethylacetyl)amino]]-1H-indole, m.p. 152°–155° C.

ANALYSIS: Calculated for $C_{21}H_{23}FN_2O_2$: 71.17% C 6.54% H 7.90% N Found: 71.20% C 6.60% H 7.78% N

EXAMPLE 19

N-(t-Butoxycarbonylamino)-1H-indole

To a stirred solution of 10.0 g of N-aminoindole in 50 ml of dry THF was added 18.2 g of di-t-butyl dicarbonate in 50 ml of dry THF. The mixture was heated to 50° C. and stirred at that temperature for 16 hours under nitrogen. The solution was concentrated to an oil and purified by HPLC to provide, after crystallization from heptane/ethyl acetate, 8.20 g of N-(t-butoxycarbonylamino)-1H-indole, m.p. 112°–116° C.

ANALYSIS: Calculated for $C_{13}H_{16}N_2O_2$: 67.22% C 6.94% H 12.06% N Found: 67.55% C 6.92% H 12.04% N

EXAMPLE 21

[N-(5-Hydroxy-1H-indol-1-yl)]-2-amino]acetamide

A solution of 5.0 g of N-(5-phenylmethoxy-1H-indol-1-yl)-2-(carbamic acid, phenylmethyl ester)acetamide (Example 8b) dissolved in 1 l of methanol was added to 1.0 g of 10% Pd on C. The suspension stirred for ½ hour under atm of hydrogen. The suspension was filtered and the filtrate concentrated to an oil. The oil was triturated with ethyl acetate, filtered and dried to provide 1.76 g of [N-(5-hydroxy-1H-indol-1-yl)-2-amino]acetamide. Recrystallization from ethanol provided material having the correct analysis for the desired compound, m.p. 190°–193° C.

ANALYSIS: Calculated for $C_{10}H_{11}N_3O_2$: 58.53% C 5.40% H 20.48% N Found: 58.33% C 5.58% H 20.21% N It should be understood that this specification and examples are set forth by way of illustration and not limitation and that various modifications and changes may be made without departing from the spirit and scope of the present invention as defined by the appended claims.

We claim:

1. A process for the preparation of the compound of Formula I

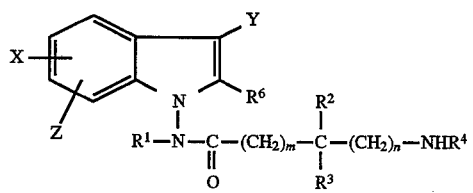

wherein

X is hydrogen, chloro, bromo, fluoro, hydroxy, loweralkoxy, arylloweralkoxy, acyloxy, loweralkylaminocarbonyloxy, diloweralkylaminocarbonyloxy, amino, loweralkylamino, diloweralkylamino, acylamino, loweralkyl or trifluoromethyl;

Y is hydrogen, loweralkyl, chloro or bromo;

Z is hydrogen, loweralkyl, loweralkoxy or halogen; or X and Z taken together can form a methylenedioxy group;

$R^1$ is hydrogen, loweralkyl, arylloweralkyl, carboxyloweralkyl, arylloweralkoxycarbonyllower-alkyl or loweralkoxycarbonylloweralkyl;

$R^2$ is hydrogen, loweralkyl or hydroxyloweralkyl;

$R^3$ is hydrogen or loweralkyl; or $R^2$ and $R^3$ together with the carbon to which they are attached form ($C_3$–$C_7$)cycloalkyl;

$R^4$ is hydrogen or loweralkyl;

$R^6$ is hydrogen, chloro, bromo, arylcarbonyl, loweralkylcarbonyl, aryl(hydroxy)loweralkyl or hydroxyloweralkyl;

m and n are independently 0 to 5;

and pharmaceutically acceptable addition salts thereof and optical or geometrical isomers or racemic mixtures thereof which process comprises reacting an aminoindole of Formula II

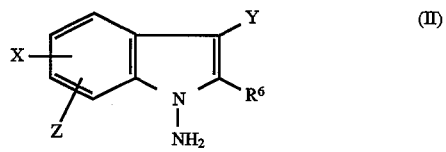

wherein X, Y, Z and $R^6$ are as defined above with a compound of Formula III

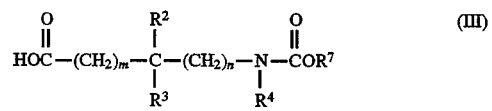

wherein $R^2$, $R^3$, $R^4$, m and n are as defined above and $R^7$ is loweralkyl or arylloweralkyl in the presence of a condensing agent to yield the compound of Formula IV

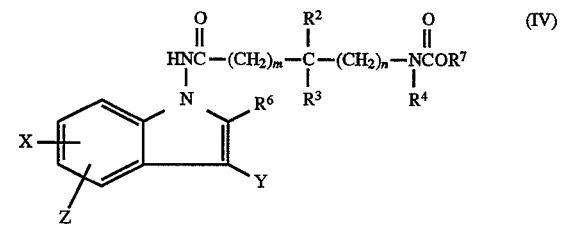

wherein X, Y, $R^2$, $R^3$, $R^4$, $R^6$, m and n are as defined above and $R^7$ is loweralkyl or arylloweralkyl; and deprotecting the compound of Formula IV and obtaining the compounds of Formula I.

2. A process for the preparation of the compound of formula (I)

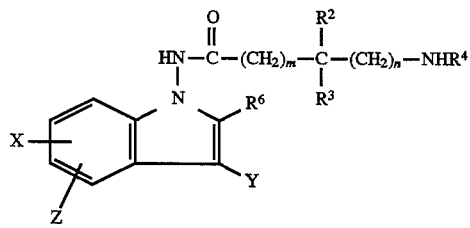

wherein

X is hydrogen, chloro, bromo, fluoro, hydroxy, loweralkoxy, arylloweralkoxy, acyloxy, loweralkylaminocarbonyloxy, diloweralkylaminocarbonyloxy, amino, loweralkylamino, diloweralkylamino, acylamino, loweralkyl or trifluoromethyl;

Y is hydrogen, loweralkyl, chloro or bromo;

Z is hydrogen, loweralkyl, loweralkoxy or halogen; or X and Z taken together can form a methylenedioxy group;

$R^4$ is hydrogen or loweralkyl; and $R^6$ is chloro, bromo which process comprises reacting a compound of Formula IV

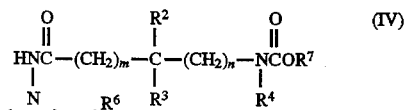

wherein

X, Z, $R^2$, $R^3$, $R^4$, m and n are as defined above, $R^6$ is hydrogen, Y is loweralkyl and $R^7$ is loweralkyl with N-chloro or N-bromosuccinamide, optionally in the presence of a catalyst and obtaining a compound of Formula VI

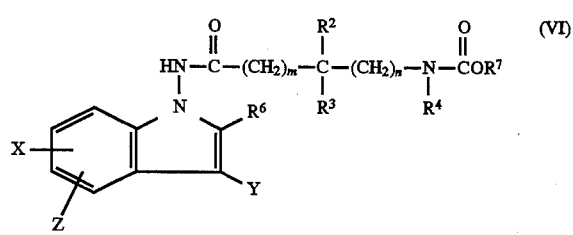

wherein $R^6$ is halogen; and deprotecting the compound of Formula VI and obtaining the compound of Formula I.

* * * * *